United States Patent [19]

Fuller et al.

[11] Patent Number: 4,679,426

[45] Date of Patent: Jul. 14, 1987

[54] WAVE SHAPE CHEMICAL ANALYSIS APPARATUS AND METHOD

[76] Inventors: Milton E. Fuller, 301 Bartlett St., Reno, Nev. 89512; Gary S. Fletcher, Jr., 8123 Sunrise Blvd., No. 224, Citrus Heights, Calif. 95610

[21] Appl. No.: 774,150

[22] Filed: Sep. 9, 1985

[51] Int. Cl.⁴ .............................................. G01N 29/02
[52] U.S. Cl. ........................................ 73/53; 73/61 R
[58] Field of Search .................... 73/53, 61 R, 61.1 R, 73/590

[56] References Cited

U.S. PATENT DOCUMENTS

| | | |
|---|---|---|
| 3,048,772 | 8/1962 | Saunders et al. |
| 3,287,638 | 11/1966 | Bolie |
| 3,489,522 | 1/1970 | McConnell |
| 3,648,513 | 3/1972 | Patterson ................................. 73/53 |
| 3,654,072 | 4/1972 | Massa .............................. 73/53 X R |
| 3,765,841 | 10/1973 | Paulson et al. |
| 4,327,587 | 5/1982 | Docekal et al. ....................... 73/590 |

Primary Examiner—Stewart J. Levy
Assistant Examiner—Joseph W. Roskos
Attorney, Agent, or Firm—Manfred M. Warren; Robert B. Chickering; Glen R. Grunewald

[57] ABSTRACT

An apparatus and method for measuring the concentration of a chemical substance in a test sample based on a technique of waveform distortion analysis is disclosed. The apparatus includes a waveform generator that generates a periodic signal, an antenna probe that transmits the signal into the test sample and receives from the test sample a corresponding periodic signal, the waveform of which has been distorted or otherwise transformed by the chemical, and a detector circuit that quantifies the transformation of the signal to determine the concentration of the chemical in the test sample. The waveform shape and frequency are selected so that the transformation is particularly responsive to the presence of a selected chemical substance, so that the magnitude of the distortion or transformation of the signal is directly related to the concentration of the selected chemical substance.

21 Claims, 5 Drawing Figures

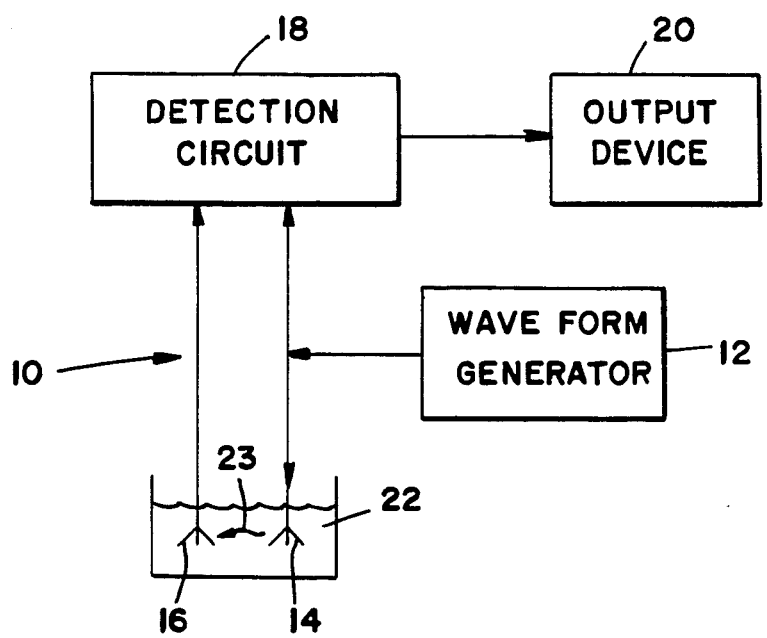
FIG_1
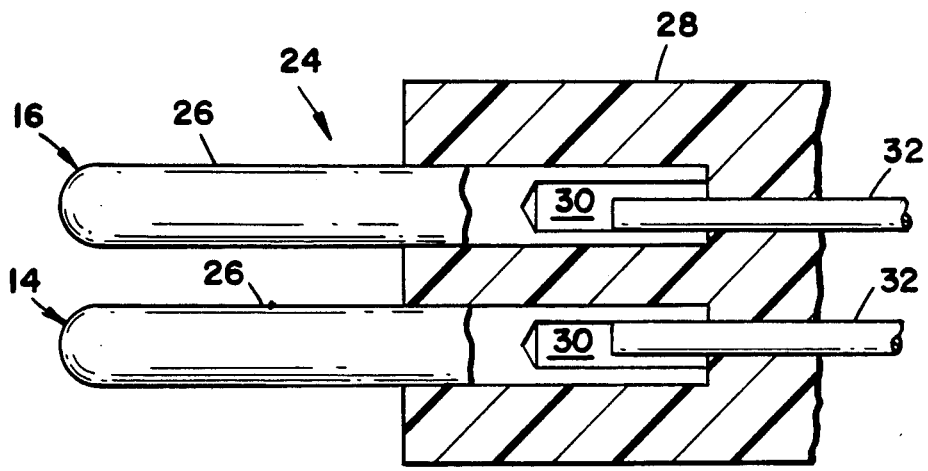
FIG_2

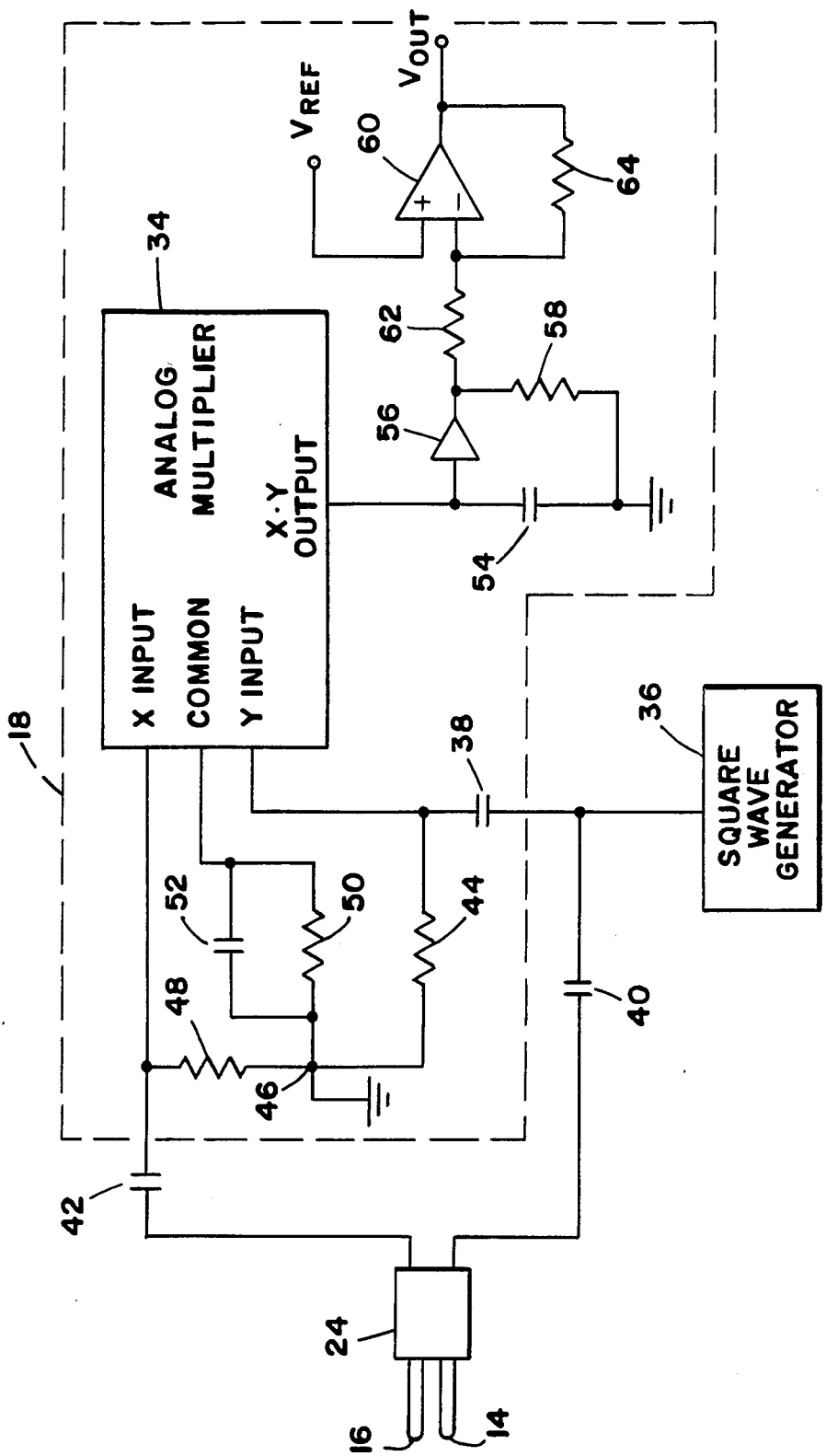
FIG_3

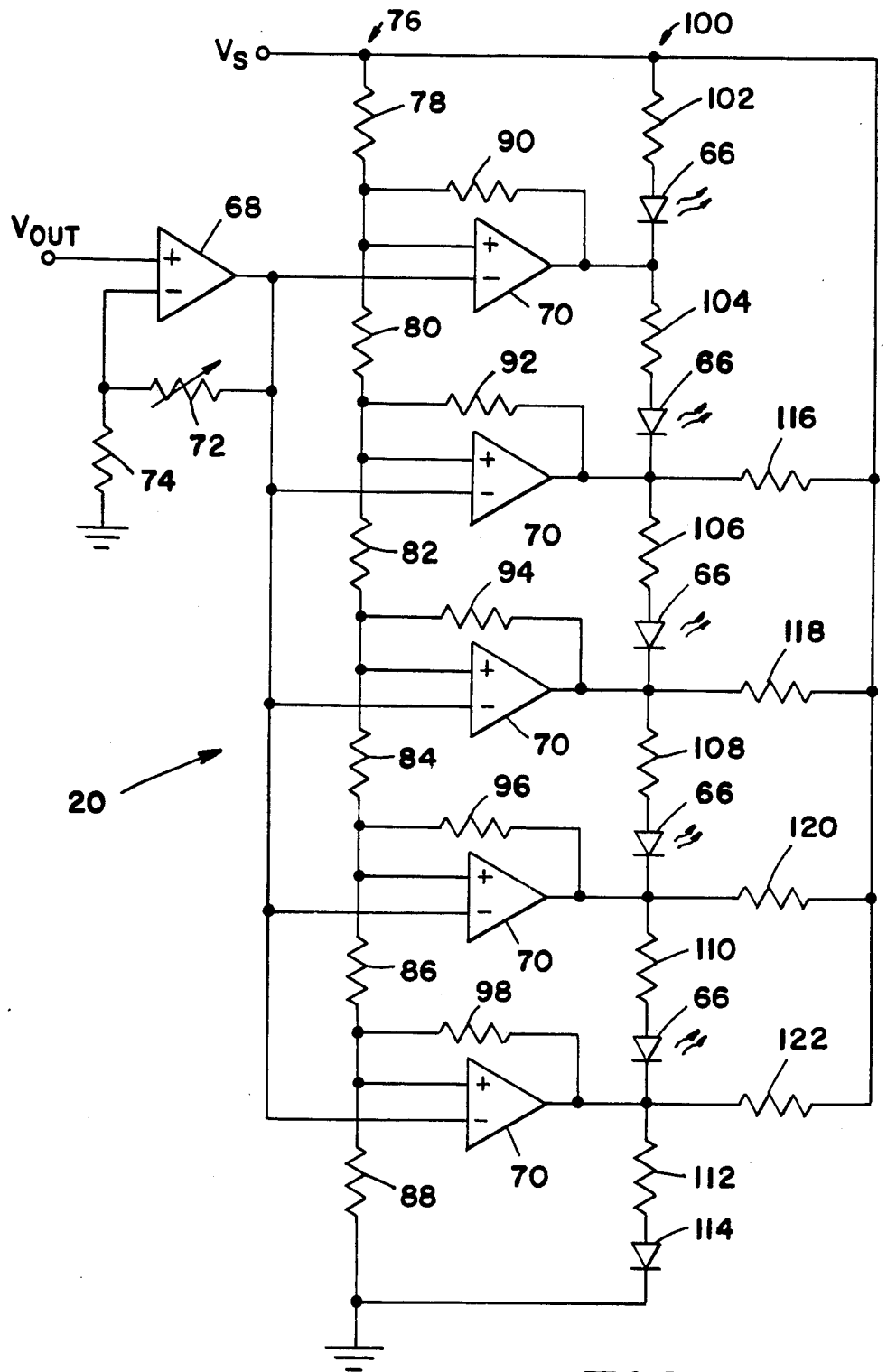
FIG_4

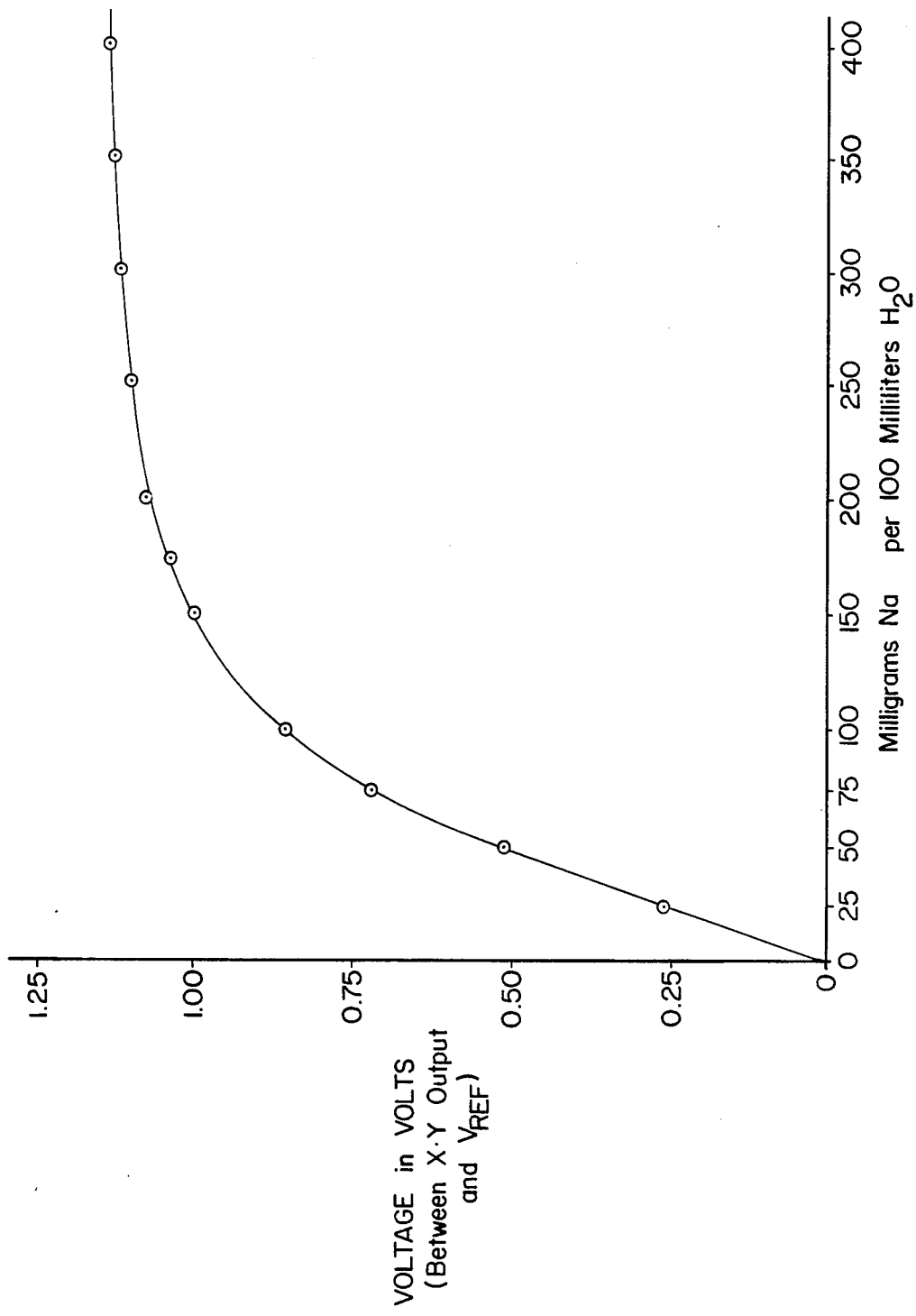
FIG_5

WAVE SHAPE CHEMICAL ANALYSIS APPARATUS AND METHOD

BACKGROUND OF THE INVENTION

1. Field of the Invention

This invention relates generally to chemical analysis apparatus, and relates more particularly to an apparatus and method for determining chemical concentration based on waveform distortion analysis.

2. Description of the Relevant Art

The public awareness of the health hazards that sodium compounds including table salt pose in food products has increased dramatically in recent years. There are a number of apparatus currently available that are capable of performing chemical analyses using a variety of techniques to measure concentrations of chemical substances such as sodium. These techniques include mass spectrophotometry, nuclear resonance, flame photometry, specific electrodes, conductivity testers, and refractometry. Unfortunately, the accuracy of these currently available apparatus is strongly dependent upon their cost. At the low end of the cost scale is the continuity tester, which measures the conductivity of a test sample to determine sodium content. Unfortunately, a continuity tester will yield inaccurately high test results when the test sample contains other conductive substances such as vinegar. What is needed is an inexpensive, but accurate, sodium measurement apparatus.

On a broader scale, there is a need for a chemical analysis apparatus that is accurate, easy to use, and inexpensive, and that responds rapidly to changes in chemical concentrations. A fiew of the many approaches to chemical analysis apparatus are described in the following U.S. Pat. Nos.: 3,048,772, issued Aug. 7, 1962 to R. K. Saunders, et al., entitled "Process for Conducting Quantitative Analysis," which discloses a nuclear magnetic resonance spectrometer; 3,287,638, issued Nov. 22, 1966 to V. W. Bolie, entitled "Method of Counting Erythrocytes Utilizing High Frequency Current," which measures the impedance variation of a solution flowing through an orifice to count red blood cells; 3,489,522, issued Jan. 13, 1970 to H. M. McConnell, entitled "Electron Spin Resonance Labeling of Biomolecules," which utilizes a radio frequency alternating magnetic field and a unidirectional magnetic field to identify biomolecules; and 3,765,841, issued Oct. 16, 1973 to Paulson, et al., entitled "Method and Apparatus for Chemical Analysis," which measures the rate of change of the conductivity of a test sample to measure the concentrations of reactive substances. Chemical analysis apparatus such as these are either very expensive, or very limited in their use.

SUMMARY OF THE INVENTION

In accordance with the illustrated preferred embodiment, the present invention provides an apparatus and method for measuring the concentration of a chemical substance in a test sample based on a technique of waveform distortion analysis.

The apparatus includes a waveform generator that generates a periodic signal, an antenna probe that transmits the signal into the test sample and receives from the test sample a corresponding periodic signal, the waveform of which has been distorted or otherwise transformed by the chemical, and a detector circuit that quantifies the transformation of the signal to determine the concentration of the chemical in the test sample.

The method includes the steps of generating a signal having a periodic waveform and transmitting that signal through the test sample, receiving the signal after it has propagated through the test sample and has been distorted or otherwise transformed by the chemical in the test sample, and detecting the magnitude of the transformation of the signal, which is directly related to the concentration of the chemical in the test sample. Another method involves the tuning of the apparatus for sensitivity to a particular chemical by selecting a frequency and waveform shape for the transmitted signal in order to maximize the distortion or transformation of the signal due to the presence of the chemical in the test sample.

The apparatus and method of the present invention are not based upon the technique of conductivity testing, or any of the other previously employed chemical analysis techniques. Instead, the chemical analysis apparatus of the present invention is based upon comparative analysis of a periodic signal transmitted through a test sample. The signal is distorted or otherwise transformed by one or more chemical substances in the test sample. The waveform shape and frequency are selected so that the transformation is particularly responsive to the presence of a selected chemical substance, so that the magnitude of the distortion or transformation of the signal is directly related to the concentration of the selected chemical substance.

In the preferred embodiment of the invention, which measures the concentration of salt in an aqueous solution, the waveform generator generates a square wave at a frequency of either sixteen or eighteen megahertz, and supplies that signal to the antenna probe. The antenna probe includes two conductive prongs protruding in parallel from a housing. The prongs act as antennas for transmitting the square wave signal into the test sample and for receiving the distorted or transformed signal from the test sample. In use, the prongs of the antenna probe are inserted into the test sample, and the square wave signal is transmitted into the test sample via one of the prongs. The waveform shape of the signal is distorted by the sodium or chloride ions as the signal propagates through the test sample. The distorted signal is received by the other prong of the antenna probe and is sent to the detector circuit for analysis.

The detector circuit responds to the transmitted and received signals to generate an output signal that is related to the magnitude of the distortion of the signal. A capacitor and resistor network supplies an "average" of the transmitted and received signals as a reference signal to a common input terminal of an analog multiplier. The analog multiplier multiplies the difference between the transmitted and reference signals by the difference between the received and reference signals to generate the output signal. An output device responds to the output signal of the detector circuit to visually indicate the presence and concentration of salt in the test sample.

The features and advantages described in the specification are not all inclusive, and particularly, many additional features and advantages will be apparent to one or ordinary skill in the art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

FIG. 1 is a block diagram of a chemical analysis apparatus according to the present invention.

FIG. 2 is a sectional view of an antenna probe utilized in the chemical analysis apparatus of FIG. 1.

FIG. 3 is a schematic view of an electronic circuit utilized in the chemical analysis apparatus of FIG. 1 for signal generation and distortion detection.

FIG. 4 is a schematic view of an output circuit utilized in the chemical analysis apparatus of FIG. 1.

FIG. 5 is a voltage curve for output from the analog multiplier of the apparatus of the present invention.

DETAILED DESCRIPTION OF THE PREFERRED EMBODIMENT

FIGS. 1 through 4 of the drawings depict the preferred embodiment of the present invention for purposes of illustration only. One skilled in the art will readily recognize from the following discussion that alternative embodiments of the structures and methods illustrated herein may be employed without departing from the principles of the invention described herein.

The preferred embodiment of the present invention is an apparatus and method for determining the concentration of sodium chloride in an aqueous solution based on waveform distortion analysis. As illustrated more generally in FIG. 1, the chemical analysis apparatus 10 of the present invention includes a waveform generator 12, a transmitting antenna 14, a receiving antenna 16, a detection circuit 18, and an output device 20. The transmitting and receiving antenna 14 and 16 are placed in contact with a test sample 22, which contains a solution to be tested for the presence of one or more selected chemical substances.

In operation, the waveform generator 12 supplies an electromagnetic signal having a periodic waveform to the transmitting antenna 14 and to the detection circuit 18. The electromagnetic signal 23 is transmitted into the test sample 22, propagates through the test sample, and is received by the receiving antenna 16. The waveform shape and frequency of the signal 23 is selected to be susceptible to distortion by the presence of the selected chemical in the test sample. As the signal 23 propagates from the transmitting antenna 14 to the receiving antenna 16, the signal is distorted or otherwise transformed by the selected chemical substance. The amount of the distortion or transformation is a function of the concentration of the selected chemical in the test sample 22. Both the undistorted transmitted signal and the distorted received signal are supplied to the detection circuit 18, which analyses the two signals to determine the magnitude of the distortion or transformation, and generates an output signal based on that analysis. The output signal is supplied to the output device 20, which visually displays the measured concentration of the selected chemical.

FIGS. 2, 3, and 4 illustrate the preferred embodiment of the chemical analysis apparatus 10, which is intended for measuring the concentration of sodium or chloride ions in an aqueous solution. FIG. 2 shows an antenna probe 24 that contains the transmitting and receiving antennas 14 and 16. Each antenna 14 and 16 is a conductive, cylindrical rod 26 extending outwardly from an insulative housing 28. At the inward end of each rod 26 is an axial cavity 30, into which is soldered a wire 32 that electrically connects the rod 26 to either the waveform generator 12 or the detection circuit 18. The axial cavity serves as a filter to help eliminate harmonics of the transmitted and received signals. The outward tips of the rods 26 are fully radiused.

In FIG. 3, the circuitry of the detection circuit 18 is illustrated. The heart of the detection circuit 18 is an analog multiplier 34, which receives the transmitted and received signals as input signals and generates an output signal that is related to the amount of distortion in the signal caused by sodium or chloride ions in the test sample. In the preferred embodiment, the waveform generator 12 is a square wave generator 36, which is coupled to a Y input terminal of the analog multiplier 34 through a capacitor 38, and is coupled to the transmitting antenna 14 of the antenna probe 24 through a capacitor 40. The receiving antenna 16 of the antenna probe 24 is coupled to an X input terminal of the analog multiplier 34 through a capacitor 42. Capacitors 40 and 42 isolate the antenna probe from any direct current components of the signal 23.

A capacitor and resistor network acts as a summing circuit to supply an "average" of the transmitted and received signals to a common input terminal of the analog multiplier 34 for use as a reference signal. The capacitor and resistor network includes a resistor 44 connected between the Y input terminal and a grounded node 46, a resistor 48 connected between the X input terminal and the grounded node 46, and a resistor 50 and a capacitor 52 connected in parallel between the common input terminal and the grounded node 46.

The analog multiplier 34 in effect measures the amount of distortion between the transmitted and received signals, which is directly related to the concentration of sodium or chloride ions in the test sample 22. The analog multiplier 34 multiplies the differential voltage applied across the X input and common terminals by the differential voltage applied across the Y input and common terminals. Since the reference signal supplied by the capacitor and resistor network is intermediate in voltage between the transmitted and received signals, one differential input to the analog multiplier 34 is positive and the other is negative. Thus, the X times Y product output signal is inversely related to the difference between the transmitted and received signals, and is, thus, inversely related to the concentration of sodium or chloride ions in the test sample 22.

The output signal of the analog multiplier 34 is conditioned and then supplied to the output device 20. A capacitor 54 smooths the pulses and irregularities in the output signal of the analog multiplier 34 to supply a stable, direct current signal to a buffer 56. The output terminal of the buffer 56 is coupled to ground through a resistor 58 and to the inverting input terminal of an operational amplifier 60 through another resistor 62. The operational amplifier 60 is configured as an inverting amplifier with a reference voltage, Vref, supplied to its non-inverting input terminal, and a resistor 64 coupled to feedback the output, Vout, to the inverting input terminal. Since the operational amplifier 60 is configured as an inverting amplifier, the output signal of the operational amplifier 60, Vout, is directly related to the concentration of sodium or chloride ions in the test sample 22.

As shown in FIG. 4, the output device 20 receives the output signal of the operational amplifier 60, Vout, and, if the measured concentration of sodium or chloride ions is high enough, activates one of five light emitting diodes 66. The output device 20 includes a non-inverting operational amplifier 68, and five operational amplifiers 70 configured as comparators. An adjustable resistor 72 is connected to feedback the output of the operational amplifier 68 to its inverting input terminal, which also is coupled to ground through a resistor 74. The output signal of the detection circuit 18, Vout, is supplied to the non-inverting input terminal of the operational amplifier 68. The output terminal of the operational amplifier 68 is connected to the inverting input terminals of the five comparator operational amplifiers 70. A resistor ladder 76 consisting of six resistors 78, 80, 82, 84, 86, and 88 is coupled between a supply voltage, Vs, and ground. Each of the five internal nodes of the resistor ladder 76 is connected to the non-inverting input terminal of one of the comparator operational amplifiers 70. Resistors 90, 92, 94, 96, and 98 are connected as feedback resistors between the output terminal of each comparator operational amplifier 70 and its non-inverting input terminal. A resistor and diode ladder 100 consisting of six resistors 102, 104, 106, 108, 110, and 112 and six diodes 66 and 114 is coupled between the supply voltage and ground. Each of the five internal nodes of the resistor and diode ladder 100 is connected to the output terminal of one of the comparator operational amplifiers 70. The output terminals of four of the comparator operational amplifiers 70 are coupled to the supply voltage via pull-up resistors 116, 118, 120, and 122, respectively.

The output signal of operational amplifier 68 acts in cooperation with the resistor ladder 76 and the comparator operational amplifiers 70 to turn on the appropriate light emitting diode (LED) 66. Assume, for example, that the output voltage of the operational amplifier 68 is less than the voltage at the node between resistors 80 and 82, but greater than the voltage at the node between resistors 82 and 84. This will cause the upper two comparator operational amplifiers 70 to supply positive output voltages, while causing the lower three comparator operational amplifiers 70 to supply negative output voltages. Current will flow through resistor 106, causing the middle LED 66 to light. The other LED's 66 will not light because no current will flow through resistors 102, 104, 108, and 110.

In order to tune the sensitivity of the apparatus to a selected chemical, the waveform shape and frequency of the transmitted signal are selected so that the distortion or transformation of the signal is particularly responsive to the presence of the selected chemical. Since it is difficult to predict how various chemical substances will respond, the selection process is largely empirical. The first step in the selection process is to determine at which frequencies a chemical substance causes a maximum amount of distortion in a square wave signal. The antenna probe is inserted into a test sample containing a representative amount of the selected chemical substance. Then, the distortion of the square wave signal is monitored while varying the frequency of the square wave signal through a range of frequencies somewhere between ten and one hundred megahertz. The distortion can be monitored by examining the output signal of the analog multiplier, or by displaying the Lissajous patterns of the analog multiplier differential input signals on an oscilloscope and looking for complex or distorted patterns.

Most likely, several frequencies will produce a peak in the magnitude of the distortion of the square wave signal. It is advantageous to repeat the above process for several of the chemical substances most likely to be found in test samples in company with the selected chemical substance. Some of the frequency peaks of the companion substances may approach or coincide with some of the frequency peaks of the selected substance. By choosing an isolated frequency peak of the selected substance, interference and false readings due to the companion substances will not occur. It has been found that square wave signals at frequencies of about sixteen and eighteen megahertz are good choices for the measurement of concentrations of sodium chloride in an aqueous solution.

Once a frequency is determined, the waveform shape of the transmitted signal can be varied to investigate whether other waveforms are more susceptible to distortion by the chemical substance. Combinations of multiple signals with different frequencies and waveforms can also be investigated. The goal is to select a signal that is distorted by the presence of the selected chemical substance, but is not distorted by the presence of companion chemical substances that may be in the test sample in actual operation.

In addition to selecting the waveform shape and frequency of the transmitted signal, the component values of the capacitor and resistor network are also selected to tune the sensitivity of the apparatus to the selected chemical. This selection process is also empirical, and should be coordinated with the selection of the transmittal signal. Again, the distortion can be monitored by examining the output signal of the analog multiplier, or by displaying the Lissajous patterns of the analog multiplier differential input signals on an oscilloscope and looking for complex or distorted patterns.

EXAMPLES

The following table lists the component values of the capacitors and resistors employed in apparatus constructed in accordance with the present invention and used to measure the concentration of sodium chloride:

| | |
|---|---|
| capacitors 38, 40, 42 | 0.01 microforad |
| resistor 44 | 2000 ohm |
| resistor 50 | 1000 ohm |
| capacitor 52 | 0.68 microfarad |
| capacitor 54 | 2.2 microfarad |
| resistor 58 | 5100 ohm |
| resistor 62, 64 | 100,000 ohm |
| resistor 72 | 5000 ohm, variable |
| resistor 74 | 1000 ohm |
| resistor 78 | 22,000 ohm |
| resistor 80 | 4700 ohm |
| resistor 82 | 8200 ohm |
| resistor 84 | 12,000 ohm |
| resistor 86 | 8200 ohm |
| resistor 88 | 24,000 ohm |
| resistor 90, 92, 94, 96, 98 | 470,000 ohm |
| resistor 102 | 470 ohm |
| resistor 104 | 820 ohm |
| resistor 106, 108, 110, 112 | 470 ohm |
| resistor 116, 118, 120, 122 | 10,000 ohm |

The distance between antennas 14 and 16 was set at 0.80 inches. The areas of antennas were too small to reliably calculate the spacing which would produce the best efficiency, but signal peaks were observed at several spacings as the antennas were separated. The selected spacing was believed to be a fractional multiple of the transmission frequency which would enhance efficiency, although other spacings are acceptable in connection with the apparatus and method of the present invention.

FIG. 5 illustrates the output voltage, measured between the X times Y product output signal and the reference voltage, $V_{REF}$, as the concentration of sodium is increased in 100 milliliters of water. As will be seen, the curve would essentially be a straight line if plotted on a logarithmic scale. It was found that extremely high reproduceability could be achieved in connection with these data, making it possible to accurately detect the presence of Na and its concentration in milligrams per 100 milliliters of solution.

The curve of FIG. 5 was generated by employing a transmitted signal of 16 megahertz. The greatest sensitivity to distortion for chloride ions was found by testing sodium chloride and potassium chloride to occur at 17.75 megahertz. This was determined by the empirical techniques set forth above. Sodium chloride also will distort by the transmitted square wave signal at about 18 megahertz, and 42.50 megahertz. The 17.75 megahertz frequency is somewhat better than 16 megahertz. Use of 17.75 megahertz has the advantage of being somewhat sensitive to the common table salt substitute, potassium chloride. Since transmitting a signal of 17.75 megahertz requires a custom transmitter, a signal of 18.00 megahertz can be used in commercial, economically priced "salt meter."

As will be apparent it would be possible to use paired oscillators for greater selectivity as to the ion being sensed.

The sodium chloride detector also was used with vinegar, sugar, alcohol and various starch solutions and produced outputs indicating that there was no sodium chloride present. It did not, therefore, give false positive readings in such solutions, including heavily ionized solutions.

When mixtures of sodium chloride and vinegar, sugar, starch, etc. were measured, the apparatus of the present invention could sense the presence and accurately measure the concentration of sodium chloride in such solutions.

Using the method of the present invention, sensitive transmission frequencies were also obtained for potassium chloride, sugar, alcohol, water and vinegar. The component values of the capacitors and resistors for the sodium chloride detector remained the same, and the following distortion sensitive transmission frequencies were found:

| Compound | Megahertz |
|---|---|
| Potassium chloride | 17.75, 35.70 |
| Sugar | 44.3, 44.6, 50.0 |
| Vodka | 16.62, 35.5, 35.95 |
| Water | 19.80, 32.05, 36.31, 35.6, 44.3, 50.0 |
| Vinegar | 20.4 |

Further refinement and selectivity with respect to these compounds is believed possible by adjusting the wave form and/or the resistance and capacitance of the circuit.

As will be apparent, therefore, the apparatus of the present invention also appears to be well suited for computer implementation to perform complex chemical analysis. A rapid series of signals at selected frequencies can be transmitted with corresponding circuit variations, if required, to enable a high degree of selectivity and a large range of chemical compounds to be sensed, measured, stored and then output using the apparatus of the present invention and a microprocessor controller.

From the above description, it will be apparent that the invention disclosed herein provides a novel and advantageous apparatus and method for determining chemical concentration based on waveform distortion analysis. The foregoing discussion discloses and describes merely exemplary methods and embodiments of the present invention. One skilled in the art will readily recognize from such discussion that various changes, modifications and variations may be made therein without departing from the spirit and scope of the invention. Accordingly, the disclosure of the present invention is intended to be illustrative, but not limiting, of the scope of the invention, which is set forth in the following claims.

What is claimed is:

1. An apparatus for measuring the concentration of a chemical in a test sample, said apparatus comprising:

electromagnetic waveform generation means for generating an electromagnetic signal having a periodic waveform of known shape;

antenna means coupled to said waveform generation means for transmitting said electromagnetic signal into the test sample and for receiving a corresponding periodic electromagnetic signal having a waveform with a shape changed from said known shape as a result of propagation of said electromagnetic signal through the test sample; and detection means coupled to said antenna means and responsive to the transmitted and received electromagnetic signals for quantifying the change in shape of said received electromagnetic signal with respect to said known shape of said transmitted electromagnetic signal, said detection means further being formed to determine the concentration of the chemical in the test sample by correlation of the magnitude of the change in shape relative to a known concentration of the chemical from calibration test samples.

2. An apparatus as recited in claim 1 wherein,
said waveform generation means is operable for generating an electromagnetic signal having a shape and frequency selected with reference to the chemical for which concentration is to be measured in order to enhance the magnitude of said change in shape.

3. An apparatus as recited in claim 2 wherein, said waveform generation means includes a square wave oscillator.

4. An apparatus as recited in claim 1 wherein,
said antenna means includes two conductive prongs protruding from a housing with one of said prongs being operable for transmitting said electromagnetic signal into the test sample and the other one of said prongs being operable for receiving said electromagnetic signal from the test sample; and each of said prongs further being generally cylindrical in shape and including a solid end that protrudes from said housing for insertion into the test sample, said prongs further being formed with a hollow cavity disposed opposite said solid end for receiving an electrical conductor for connection to at least one of said waveform generation means and said detection means.

5. An appartus as recited in claim 1 wherein, said detection means includes summing means for generating a reference signal having a periodic waveform by combining said transmitted electromagnetic signal and said received electromagnetic signals, and said detection means includes signal processing means coupled to receive said transmitted electromagnetic signal, said received electromagnetic signal, and said reference signal for generating an output signal related to the concentration of the chemical in the test sample by multiplying the voltage differential between said transmitted electromagnetic signal and said reference signal by the voltage differential between said received electromagnetic signal and said reference signal.

6. An apparatus as recited in claim 5 wherein, said detection means further includes output means responsive to said output signal for displaying an indication of the concentration of the chemical in the test sample.

7. An apparatus as recited in claim 1 wherein, said waveform generation means is isolated from said antenna means by a capacitor to prevent direct current flow through the test sample.

8. An apparatus as recited in claim 1 wherein, said detection means is isolated from said antenna means by a capacitor to prevent direct current flow through the test sample.

9. An apparatus for measuring the concentration of sodium chloride in a test sample, said apparatus comprising:
waveform generation means for generating an electromagnetic signal having a periodic substantially square waveform and a frequency selected with reference to sodium chloride in order to enhance the magnitude of the change in shape of said waveform during propagation in the test sample;
antenna means coupled to said waveform generation means for transmitting said electromagnetic signal into the test sample and for receiving a corresponding periodic electromagnetic signal from the test sample, wherein the waveform of said electromagnetic signal is changed in shape by said sodium chloride as said electromagnetic signal propagates through the test sample; and
detection means responsive to the transmitted and received electromagnetic signals for quantifying the change in shape of said electromagnetic received signal with respect to said transmitted electromagnetic signal to determine the concentration of sodium chloride in the test sample, wherein the magnitude of the change of shape is related to the concentration of sodium chloride in the test sample.

10. An apparatus for measuring the concentration of sodium chloride as recited in claim 9, wherein, said transmitted electromagnetic signal has a frequency of between fifteen and nineteen megahertz.

11. An apparatus for measuring the concentration of sodium chloride as recited in claim 10 wherein,
said transmitted electromagnetic signal has a frequency substantially equal to sixteen megahertz.

12. An apparatus for measuring the concentration of sodium chloride as recited in claim 10 wherein,
said transmitted electromagnetic signal has a frequency substantially equal to eighteen megahertz.

13. An apparatus for measuring the presence of a chemical in a test sample, said apparatus comprising:
electromagnetic signal generation means formed for generating an electromagnetic signal having a periodic waveform and a shape and frequency selected with reference to the chemical to be measured;
electromagnetic signal transmission means coupled to said electromagnetic signal generation means for transmitting said electromagnetic signal into the test sample;
electromagnetic signal receiving means spaced apart from said transmission means for receiving said electromagnetic signal after it has propagated through the test sample for distortion of the shape of said electromagnetic signal upon the presence of the chemical in the test sample; and
detection means responsive to the transmitted and received electromagnetic signals for detecting the distortion of the shape of said electromagnetic signal upon the presence of the chemical in the test sample and indicating the presence of the chemical upon detecting distortion of the shape of said electromagnetic signal.

14. A method for detecting the presence of a chemical in a test sample, said method comprising the steps of:
generating an electromagnetic signal having a periodic waveform and transmitting said electromagnetic signal through a portion of the test sample;
receiving said electromagnetic signal after it has passed through the test sample; and
detecting any change in shape of said electromagnetic signal, as a result of passing through the test sample and correlating said transformation of the shape to the presence of the chemical in the test sample.

15. A method as recited in claim 14 wherein, said step of generating an electromagnetic signal includes the step of generating an electromagnetic signal having a shape and frequency selected with reference to the chemical to be measured in order to enhance the magnitude of the transformation.

16. A method as recited in claim 14 wherein,
said step of detecting the change in shape of said electromagnetic signal includes the steps of generating a reference signal having a periodic waveform by combining said transmitted and received electromagnetic signals, and generating an output signal related to the concentration of the chemical in the test sample by multiplying the voltage differential between said transmitted and reference electromagnetic signals by the voltage differential between said received electromagnetic signal and said reference signal.

17. A method for tuning an apparatus for measuring the concentration of a chemical in a test sample, wherein said apparatus includes electromagnetic waveform generation means for generating an electromagnetic signal having a periodic waveform of known shape, includes antenna means coupled to the waveform generation means for transmitting the electromagnetic signal into the test sample and for receiving from the test sample a periodic electromagnetic signal having a changed shape from said known shape that results from the electromagnetic signal propagating through the test sample, and includes detection means responsive to the transmitted and received electromagnetic signals for quantifying the change in shape of the electromagnetic signal, said method comprising the steps of:
inserting the antenna means into a test sample containing a representative amount of the chemical;
monitoring the amount of change in shape of the received electromagnetic signal with respect to the transmitted electromagnetic signal while varying the frequency of the transmitted electromagnetic signal through a range of frequencies;

selecting for use as the frequency of the transmitted electromagnetic signal in using the apparatus to measure the concentration of the chemical that frequency which causes the greatest amount of change in shape of the signal due to the presence of the chemical in the test sample; and monitoring the amount of change of shape of the received electromagnetic signal with respect to the transmitted electromagnetic signal while varying the waveform shape of the transmitted electromagnetic signal, and selecting for use as the waveform shape of the transmitted electromagnetic signal in using the apparatus to measure the concentration of the chemical that waveform shape which causes the greatest amount of change of shape of the electromagnetic signal due to the presence of the chemical in the test sample.

18. A method for measuring the concentration of sodium chloride in a test sample comprising the steps of:

generating an electromagnetic signal having a periodic waveform of known shape and a frequency of between about fifteen and nineteen megahertz;

transmitting said electromagnetic signal through a portion of said test sample;

receiving said electromagnetic signal after it has passed through said test sample;

detecting changes in shape of the received electromagnetic signal as compared to said known shape; and quantifying said changes in shape and correlating the quantified changes in shape with a concentration of sodium chloride.

19. A method for measuring the concentration of sodium chloride in a test sample, as recited in claim 18 wherein, said step of generating an electromagnetic signal includes the step of generating an electromagnetic signal having a substantially square shape.

20. A method as recited in claim 18 wherein, said signal has a frequency substantially equal to sixteen megahertz.

21. A method as recited in claim 18 wherein, said electromagnetic signal has a frequency substantially equal to eighteen megahertz.

* * * * *